United States Patent
Bingham (10) Patent No.: US 10,794,873 B2
(45) Date of Patent: Oct. 6, 2020

(54) SIGNAL PROCESSING FOR ULTRASOUND IMAGING SYSTEMS

(71) Applicant: The Boeing Company, Chicago, IL (US)

(72) Inventor: Jill Paisley Bingham, Seattle, WA (US)

(73) Assignee: The Boeing Company, Chicago, IL (US)

( * ) Notice: Subject to any disclaimer, the term of this patent is extended or adjusted under 35 U.S.C. 154(b) by 1221 days.

(21) Appl. No.: 15/089,737

(22) Filed: Apr. 4, 2016

(65) Prior Publication Data

US 2017/0281137 A1 Oct. 5, 2017

(51) Int. Cl.

| | |
|---|---|
| *G01N 29/44* | (2006.01) |
| *A61B 8/08* | (2006.01) |
| *A61B 8/00* | (2006.01) |
| *G01H 7/00* | (2006.01) |
| *G01H 3/10* | (2006.01) |
| *G01N 29/04* | (2006.01) |
| *G01N 29/06* | (2006.01) |

(52) U.S. Cl.
CPC ......... *G01N 29/4463* (2013.01); *A61B 8/461* (2013.01); *A61B 8/5269* (2013.01); *A61B 8/54* (2013.01); *G01H 3/10* (2013.01); *G01H 7/00* (2013.01); *G01N 29/048* (2013.01); *G01N 29/069* (2013.01); *G01N 29/449* (2013.01); *G01N 29/4445* (2013.01)

(58) Field of Classification Search
CPC ...... G01N 29/04; G01N 29/048; G01N 29/06; G01N 29/0654; G01N 29/069; G01N 29/07; G01N 29/32; G01N 29/44; G01N 29/4445; G01N 29/4463; G01N 29/449; G01H 3/10; G01H 7/00
USPC .......................... 73/597, 598, 602, 627, 645
See application file for complete search history.

(56) References Cited

U.S. PATENT DOCUMENTS 5,665,907 A * 9/1997 Sheen .................... G01N 29/11
73/159
2017/0176621 A1 * 6/2017 Valero .................... E21B 47/14

OTHER PUBLICATIONS

Belhedi et al., Noise Modeling and Uncertainty Propagation for TOF Sensors, CEA, LIST, LVIC, Universite de Tunis El Manar, ENTI, SITI.

* cited by examiner

*Primary Examiner* — Benjamin R Schmitt
(74) *Attorney, Agent, or Firm* — Duft & Bornsen, PC (57) ABSTRACT

Systems and methods are provided for selectively utilizing ultrasound data to quantify a part being scanned. One embodiment is a system that includes an ultrasonic wave generator configured to induce ultrasonic waves at locations along a part being scanned, and a controller. The controller is configured to operate the ultrasonic wave generator to collect data points that each indicate amplitude data and time-of-flight data of an ultrasonic wave at the part, to calculate a standard deviation of the time-of-flight data of the data points ($\sigma_{tof}$), to utilize the amplitude data to quantify the part if $\sigma_{tof}$ is less than a threshold value, and to flag the data points in memory as including noise if $\sigma_{tof}$ is greater than the threshold value.

20 Claims, 6 Drawing Sheets

AMPLITUDE

TIME OF FLIGHT

SIGNAL PROCESSING FOR ULTRASOUND IMAGING SYSTEMS

FIELD

The disclosure relates to the field of imaging, and in particular, to ultrasonic imaging.

BACKGROUND

Ultrasonic imaging may be utilized for a variety of purposes. For example, ultrasonic imaging may be performed upon a part/object in order to image a hidden interior or external surfaces of the part. In this manner, ultrasonic imaging may be used to ensure that the internal composition of the part meets with specific standards of quality. In such systems, ultrasonic waves may be generated at a surface of a part and transmitted through the part. As the waves are reflected from an acoustic impedance mismatch (e.g., a back surface anomaly or other part geometry) of the part towards an imaging system, the waves may be analyzed in order to quantify properties of the part being imaged.

One technique for imaging a part via ultrasound is known as a "C-scan." A C-scan is a nondestructive testing technique that is used to determine the internal properties of a part/object. During a C-scan, the part is probed with ultrasonic waves at each of multiple locations along its surface. The ultrasonic waves reflect within the part and return for detection. In this manner, the ultrasonic waves received at each of multiple locations on the part may be analyzed in order to form a pixel-by-pixel image/scan of a feature of the part.

Unfortunately, in many parts, characteristics such as porosity and part geometry may attenuate the strength of the ultrasonic wave as it travels through the part. Hence, it may become difficult to distinguish a returning ultrasonic wave from random noise (or scattered energy). If random noise is sampled instead of the returning ultrasonic wave, it degrades the quality of analysis performed upon the part (i.e., because data used in the analysis is inaccurate). Thus, technicians continue to strive to use enhanced techniques for ultrasonic imaging that address this issue.

SUMMARY

Embodiments described herein are capable of determining when an ultrasound image of an object is likely to be the result of random noise. If the image is likely to be the result of random noise, embodiments herein prevent the image from being used to quantify the object being scanned. Specifically, embodiments described herein are capable of detecting that the time-of-flight data for the scan is similar to random noise, and then flagging the scan as including noise. This helps to prevent the scan from being used to inaccurately quantify the object being imaged.

One embodiment is a system that includes an ultrasonic wave generator configured to induce ultrasonic waves at locations along a part being scanned, and a controller. The controller is configured to operate the ultrasonic wave generator to collect data points that each indicate amplitude data and time-of-flight data of an ultrasonic wave at the part, to calculate a standard deviation of the time-of-flight data of the data points ($\sigma_{tof}$), to utilize the amplitude data to quantify the part if $\sigma_{tof}$ is less than a threshold value, and to flag the data points in memory as including noise if $\sigma_{tof}$ is greater than the threshold value.

Another embodiment is a method for selectively utilizing ultrasound data. The method includes operating an ultrasonic wave generator to induce ultrasonic waves at each of multiple locations along a part being scanned, collecting data points that each indicate amplitude data and time-of-flight data of an ultrasonic wave at the part, calculating a standard deviation of the time-of-flight data for the data points ($\sigma_{tof}$), utilizing the amplitude data to quantify the part if $\sigma_{tof}$ is less than a threshold value, and flagging the data points in memory as including noise if $\sigma_{tof}$ is greater than the threshold value.

Another embodiment is a further system for utilizing ultrasound data. The system includes a memory, an interface, and a controller. The controller is configured to operate the interface to retrieve a scan representing a part that has been inspected via ultrasonic imaging, to populate the memory with time-of-flight data and amplitude data for each of multiple data points within the scan, to calculate a standard deviation of the time-of-flight data for the data points ($\sigma_{tof}$), and to calculate a threshold value based on a standard deviation of random (e.g., white-noise) time-of-flight data. The controller is further able to and to selectively perform signal processing on the data points by, if $\sigma_{tof}$ is less than the threshold value: generating a report quantifying the part based on the amplitude data for the data points and storing the report in the memory, and if $\sigma_{tof}$ is greater than the threshold value: updating the memory to flag the scan as including noise.

Other exemplary embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

DESCRIPTION

The figures and the following description illustrate specific exemplary embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

The following FIGS. describe techniques and systems that utilize ultrasonic scanning/imaging in order to analyze the internal properties of parts (e.g., newly manufactured multi-layer composite parts being analyzed during quality control testing). These techniques and systems are capable of reviewing data points acquired in a scan of a part, and determining whether those data points indicate that random noise was unintentionally sampled during the scan. If too much random noise was sampled, the data points provide an inaccurate indication of the internal properties of the part being scanned. Hence, the scan may be flagged as including too much noise (or otherwise including bad data).

Figure 1:
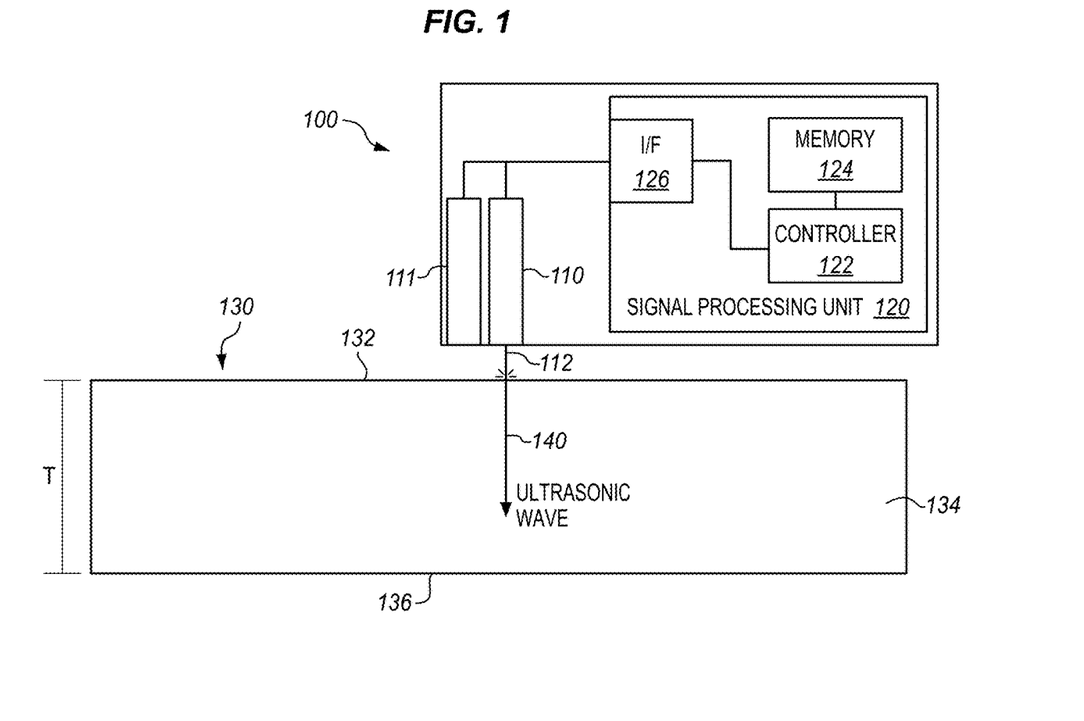
FIGS. 1-2 are diagrams illustrating an ultrasonic imaging system in an exemplary embodiment.
Figure 2:
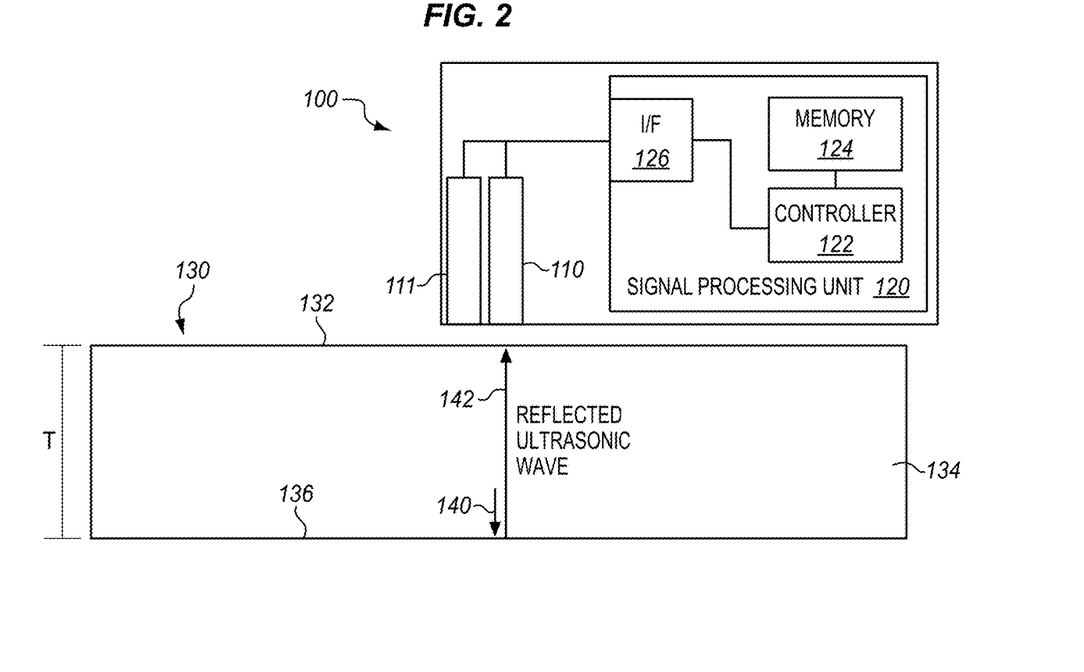

FIGS. 1-2 are diagrams illustrating an ultrasonic imaging system 100 in an exemplary embodiment. Ultrasonic imaging system 100 comprises any combination of devices and/or components capable of acquiring data points for an object/part (e.g., part 120) by inducing and/or detecting the oscillation of ultrasonic waves within that part. In this embodiment, ultrasonic imaging system 100 comprises generator 110 and signal processing unit 120. Generator 110 generates an ultrasonic wave 140 at a surface 132 of part 130 as shown in FIG. 1. If generator 110 is implemented as an ultrasonic transducer, then wave 140 may be generated by physical vibration at generator 110. Alternatively, if generator 110 comprises a laser interferometer (e.g., a confocal dual cavity laser interferometer), then generator 110 may fire a laser beam 112 at part 130 to induce ultrasonic wave 140.

The ultrasonic wave 140 travels from surface 132 of part 130 through material 134 and hits back wall 136. As used herein, back wall 136 need not be a surface at which part 130 terminates/ends, but rather comprises a location where the physical properties of part 130 (in particular, acoustic impedance) substantially change. This may include for example a part/air boundary, a fiber/resin boundary, a part/water boundary, an anomaly such as a foreign material inclusion within the part, etc. A reflected wave 142- then returns from back wall 136 for detection by system 100. In embodiments where generator 110 comprises a transducer, generator 110 may detect the return of an ultrasonic wave from back wall 136. In other embodiments, a sensor 111 may be used for this purpose.

Signal processing unit 120 analyzes data acquired by imaging system 100 in order to determine whether or not the data includes random noise. In this embodiment, signal processing unit 120 includes interface (I/F) 126 which retrieves signal data for an ultrasonic wave 142 (e.g., a reflected version of an ultrasonic wave 140 induced via generator 110), sensor 111 which detects induced ultrasonic waves, memory 124 which stores data acquired via I/F 126, and controller 122 which analyzes data maintained in memory 124. Additionally signal processing unit 120 may direct the operations of imaging system 100. In further embodiments signal processing unit 120 may be independently implemented from system 100 (e.g., as an independent computer).

I/F 126 may comprise any suitable data interface, such as a wired data connection, or a wireless transceiver. Memory 124 may comprise any component configured to store data for retrieval, including for example Random Access Memory (RAM), flash memory, a hard disk, etc. Controller 122 may be implemented, for example, as custom circuitry, as a processor executing programmed instructions, or some combination thereof. Part 130 may comprise any suitable object, component, or device capable of being imaged via ultrasound. In one embodiment, part 130 comprises a composite part made from multiple plies/tows of carbon fiber.

Figure 3:
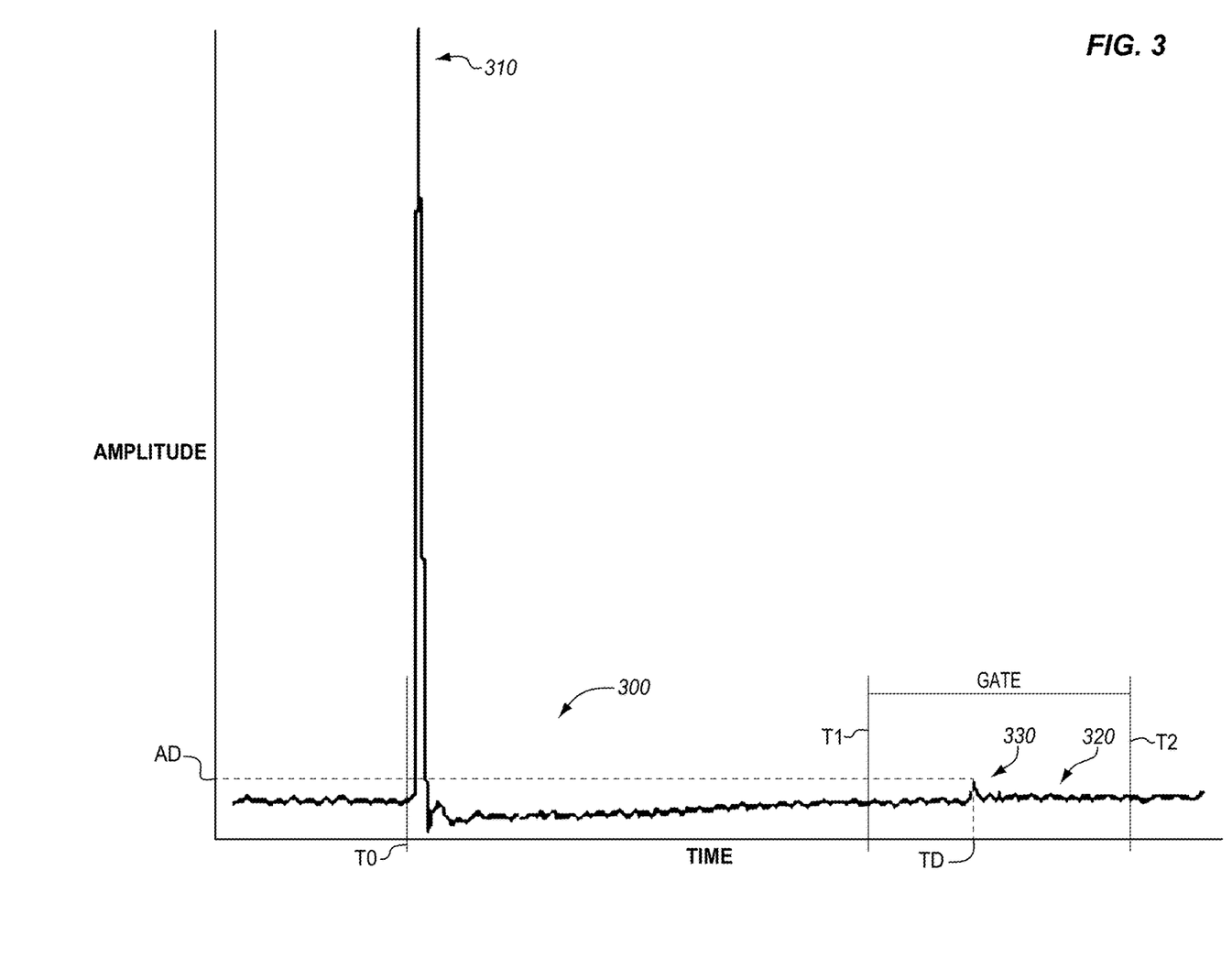
FIG. 3 is a diagram illustrating a signal acquired from an ultrasonic imaging system in an exemplary embodiment.

Details of data acquired by ultrasonic imaging system 100 are described with regard to FIG. 3. Specifically, FIG. 3 is a diagram illustrating a signal 300 acquired from ultrasonic imaging system 100 in an exemplary embodiment. As shown in FIG. 3, at some initial time $T_0$, an ultrasonic wave 140 is generated at surface 132 of part 130. This results in a large spike 310 of detected ultrasonic energy briefly after $T_0$. The ultrasonic wave 140 travels through the part 130, but attenuates as it travels (e.g., owing to the porosity of the part). Attenuation occurs regardless of porosity, but porosity enhances the level of attenuation. Based on the thickness of the part 130, an attenuated, reflected ultrasonic wave 142 is expected to return during a time period (e.g., between $T_1$ and $T_2$). Sensing of the reflected ultrasonic wave 142 is therefore gated between T1 and T2, and the highest amplitude detected between T1 and T2 is assumed to correspond to the reflected ultrasonic wave 142 after it has reflected off of the back wall 136 of the part. The time of detection ($T_D$) and the amplitude of detection ($A_D$) are recorded in memory. However, travel through the part 130 substantially reduces the power of the reflected ultrasonic wave 142. Thus, peak 330 corresponding to a reflection of wave 142 may be of a similar magnitude to random noise 320 detected by imaging system 100, and in some circumstances may even be confused with a peak of random noise 320.

Figure 4:
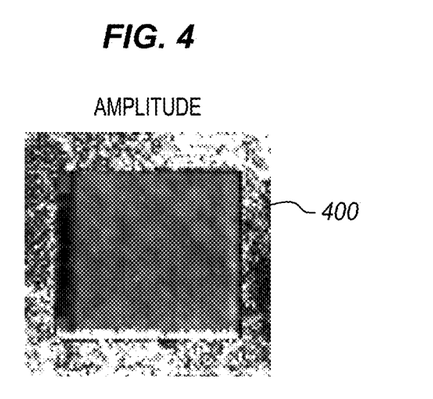
FIGS. 4-5 are images illustrating amplitude and time-of-flight data acquired during a C-scan in an exemplary embodiment.
Figure 5:
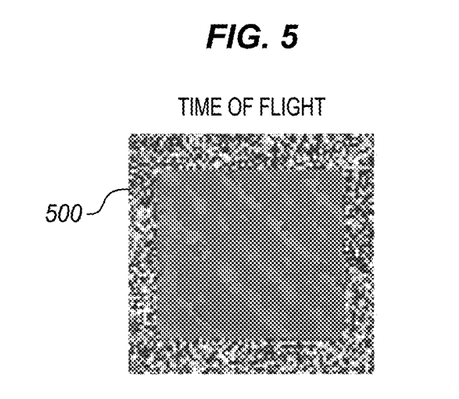
Figure 6:
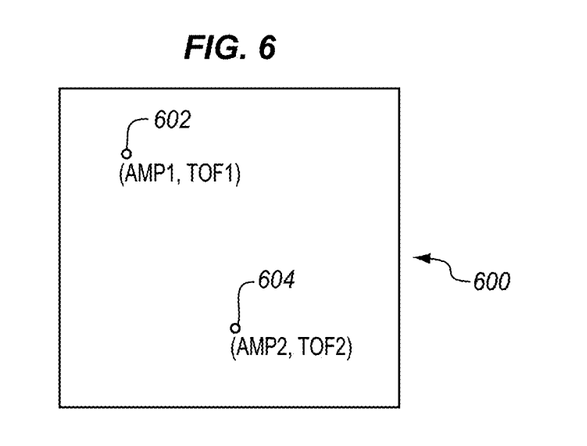
FIG. 6 is a diagram illustrating an image combining time-of-flight and amplitude data in an exemplary embodiment.

This process of detecting and recording returning ultrasonic waves may be iteratively performed at each of multiple locations on part 130, yielding time-of-flight data and amplitude data for each of multiple locations on part 130. This is known as performing a "C-scan" of the part being imaged. FIGS. 4-5 are images illustrating amplitude and time-of-flight data acquired during a C-scan in an exemplary embodiment. Specifically, FIG. 4 illustrates an image 400 formed from a C-scan that indicates amplitude values, while FIG. 5 illustrates an image 500 formed from a C-scan that indicates time-of-flight values. The amplitude and time-of-flight data may be combined such that each location on the image (e.g., as indicated by X and Y coordinates) corresponds with an amplitude value. Thus, as shown in FIG. 6, location 602 corresponds with AMP1 and TOF1, while location 604 corresponds with AMP2 and TOF2.

As used herein, the word "image" may be used to refer to a scan comprising multiple data points taken at different physical locations along a part (e.g., part 130). However, it should be noted that the term is used broadly to indicate a collection of data that quantifies a real-world object imaged by ultrasonic techniques. Thus, an "image" of part 130 may be stored and/or analyzed as an array of data points, as a table of entries, etc., and need not be stored in an image file format. Similarly, the term "pixel" may be used to refer to a single data point/sample of ultrasonic data taken at a specific location at a part.

Further details of the operation of imaging system 100 will be described with regard to method 700 of FIG. 7. Assume, for this embodiment, that imaging system 100 is being operated by signal processing unit 120, and that part 130 has been placed proximate to imaging system 100 for analysis. Thus, imaging system 100 will utilize ultrasonic techniques to image/scan part 130, and will further review this data to determine whether it has sampled random noise instead of desired ultrasonic waves. Steps 702-708 describe scanning/imaging part 130 via ultrasonic techniques, while steps 710-718 describe analysis of an acquired set of data points for part 130.

Figure 7:
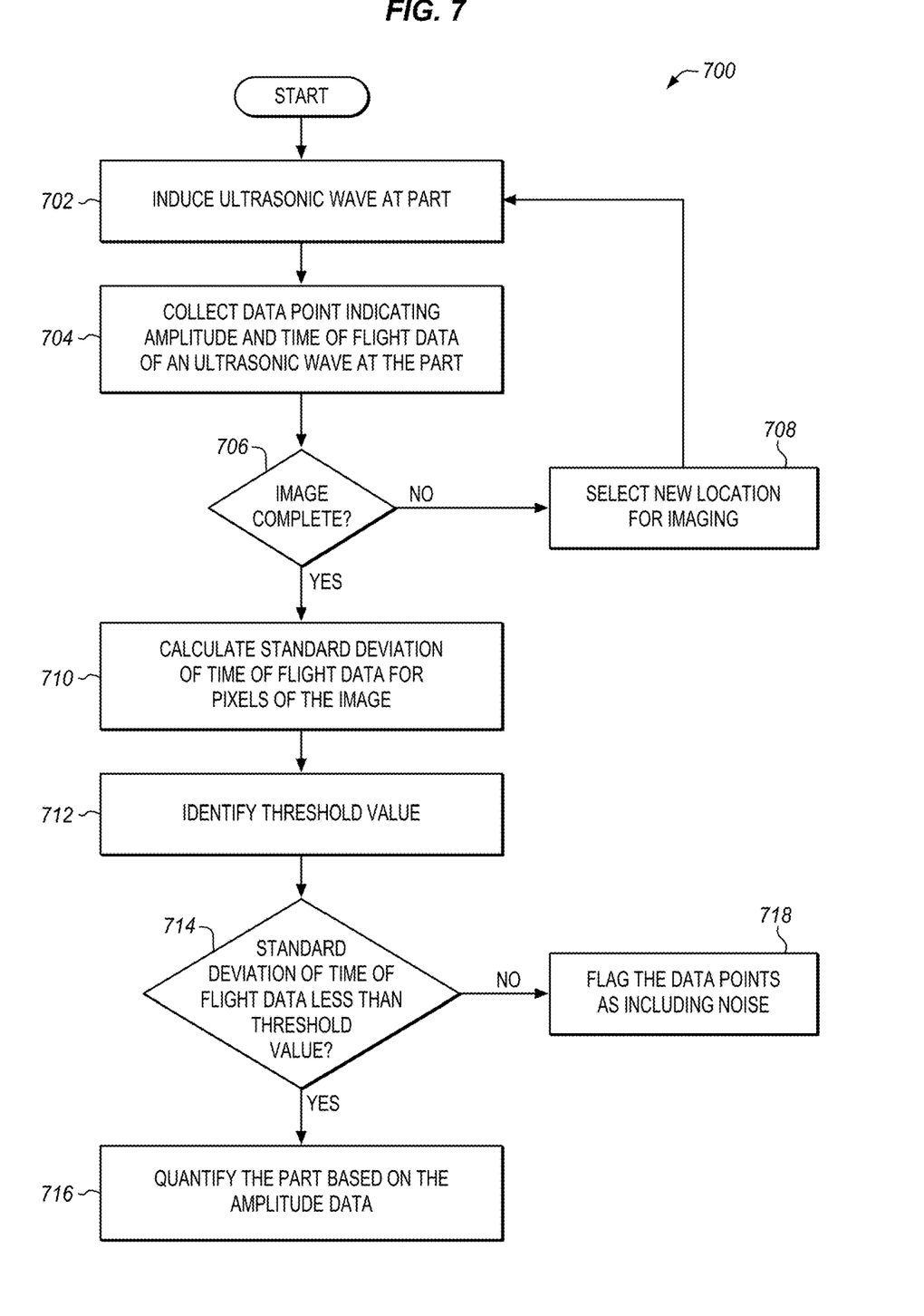
FIG. 7 is a flowchart illustrating a method of processing data acquired via an ultrasonic imaging system in an exemplary embodiment.

FIG. 7 is a flowchart illustrating a method 700 for processing data acquired by an ultrasonic imaging system in an exemplary embodiment. The steps of method 700 are described with reference to imaging system 100 of FIG. 1, but those skilled in the art will appreciate that method 700 may be performed in other systems as desired. The steps of the flowcharts described herein are not all inclusive and may include other steps not shown. The steps described herein may also be performed in an alternative order.

Controller 122 initiates the process by directing generator 110 to induce/apply an ultrasonic wave 140 at surface 132 of part 130 (e.g., via Laser Ultrasound (LUT) or via an ultrasound transducer) (step 702). The generated wave 140 travels through material 134 towards back wall 136. A reflected wave 142 returns from back wall 136 for detection by imaging system 100.

Controller 122 implements a gated detection system, such that incoming signaling is sampled over a gated period of time (e.g., one half of a second) during which the reflected ultrasonic wave 142 is expected to return from back wall 136. That is, controller 122 may acquire a waveform representing ultrasonic wave 142 during the gated time period, the waveform including a plurality of data points (each data point having corresponding amplitude data for a point in time). Controller 122 may then process the plurality of data points to collect a data point that indicates amplitude data and time-of-flight data for a feature of interest (e.g., the highest peak value during the gated time period). Thus, according to exemplary method 700, a data point is collected/selected that includes the highest peak value detected over the gated time period, and the time at which the peak value was detected (step 704). The data point may be stored in memory 124, and may be associated with the location on part 130 that was scanned. The time value therefore may indicate the transit time of the reflected ultrasonic wave 142 from inducement to detection, or may be re-scaled to fit within a range of the gated detection period (e.g., such that the beginning of the gated detection period is set to zero, while the end of the gated time period is set to a maximum time value).

Controller 122 further determines whether or not imaging/sampling/scanning of part 130 has been completed (step 706). For some parts, a resolution of many Pixels Per Inch (PPI) is desired to scan part 130. Thus, hundreds, thousands, or even millions of samples/data points may be acquired in order to form the image/scan. If not all data points have yet been acquired, controller 122 selects a new location on part 130 for scanning/imaging (step 708), and resumes steps 702-706.

Alternatively, if enough samples/data points have been acquired for the scan, then the scan/image has been completed. Hence, processing proceeds onward to step 710. In step 710, controller 122 calculates the standard deviation of time-of-flight data (herein, $\sigma_{tof}$) acquired for a number of data points within the scan. $\sigma_{tof}$ does not have to be calculated by using all of the data points acquired during the scan, but a large enough (and spatially diverse enough) set of data points should be used to ensure that an accurate and precise statistical analysis is performed.

After $\sigma_{tof}$ has been calculated, it is desirable to determine whether $\sigma_{tof}$ is indicative of random noise. To this end, controller 122 identifies a threshold value that is based off of a statistical measure of random noise (step 712). The random noise may comprise a random signal with constant power spectral density (e.g., white noise). Controller 122 may compare $\sigma_{tof}$ to the threshold value to determine whether or not $\sigma_{tof}$ is indicative of random noise. If $\sigma_{tof}$ is too similar to the threshold value (e.g., because it is highly variable), it becomes likely that the acquired samples/data points taken during scanning represent random noise.

In one embodiment, the threshold value is based on the standard deviation ($\sigma_r$) of a set of random time-of-flight values corresponding to random noise. The set of random values may be equal in size to the number of data points used to calculate $\sigma_{tof}$. The random values may be spread across all possible time-of-flight values that could be acquired during sampling. Thus, if sampling is gated to a known time period, the random values would be spread across that time period. The threshold value may be determined by adding or subtracting a specified amount to $\sigma_r$, or by multiplying/dividing $\sigma_r$ by a specific amount such as 2 or 2.5.

Next, controller 122 compares $\sigma_{tof}$ to the threshold value (step 714). If $\sigma_{tof}$ is less than the threshold value, then the time-of-flight values in the image do not vary by a notable amount, and the samples are therefore unlikely to have been the result of random noise. Thus, controller 122 may proceed to quantify part 130 based on the amplitude data (step 716). For example, controller 122 may perform calculations based upon the amplitude data stored in the image, and generate a report indicating the porosity of the part based on those calculations. The report may further detect whether the porosity of part 130 is outside of an acceptable range, and indicate that part 130 is out of tolerance in response to part 130 being outside of the range. The report may be transmitted to a user for review, shown via a display, or stored in memory 124 for later retrieval.

Alternatively, if $\sigma_{tof}$ is greater than the threshold value, then the time-of-flight data indicates that random peaks in amplitude have been sampled by system 100. Thus, controller 122 updates memory 124 to indicate that the image includes noise/bad data at a level that is unacceptable (e.g., because it would lead to an inaccurate analysis of the image) (step 718). The image may further be discarded from memory 124 or reviewed by a user, and controller 122 may attempt to re-image part 130 (e.g., using different parameters in order to attempt reduce the amount of noise being sampled).

EXAMPLES

In the following examples, additional processes, systems, and methods are described in the context of an ultrasonic imaging system 800 that analyzes an image of a composite part. The example will be described with respect to the systems and devices of FIG. 8.

Figure 8:
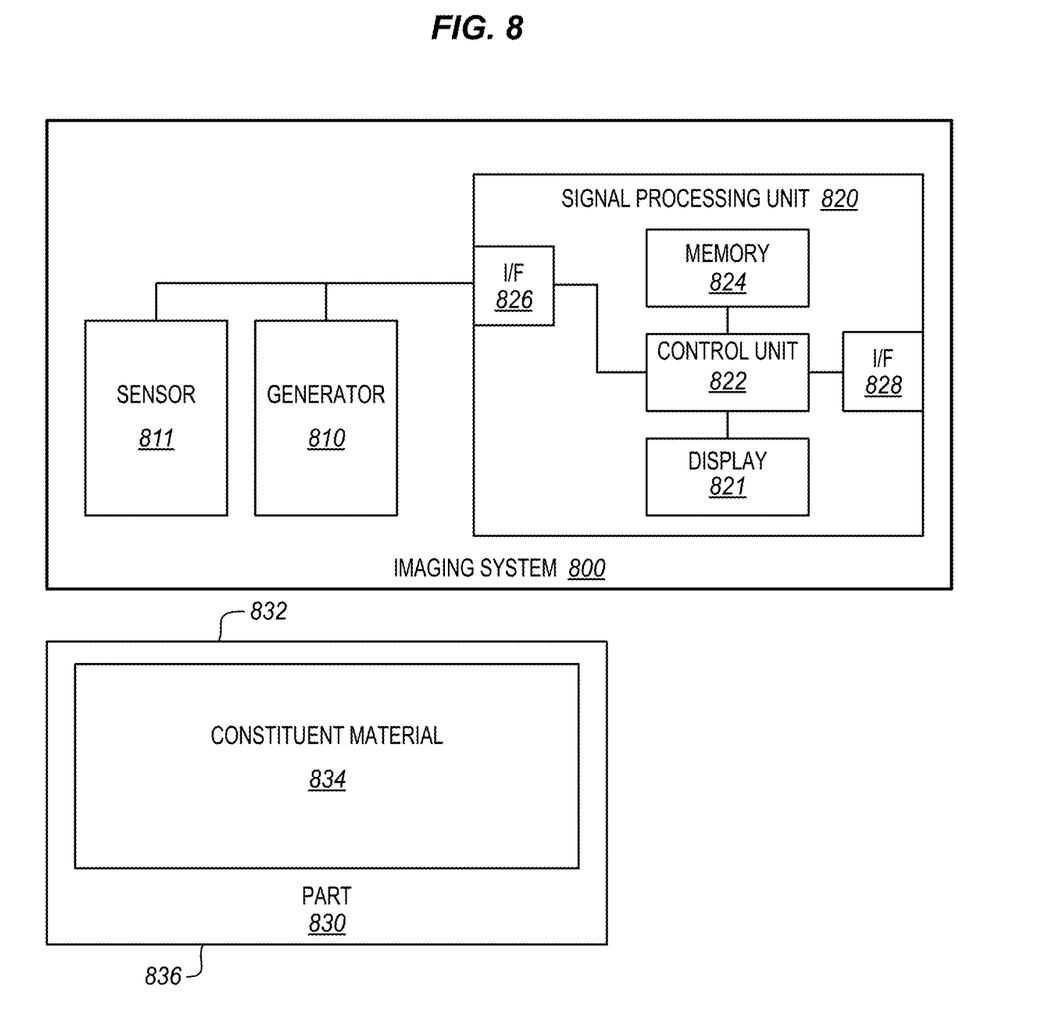
FIG. 8 is a block diagram of an ultrasonic imaging system analyzing a part in an exemplary embodiment.

FIG. 8 is a block diagram of an ultrasonic imaging system 800 analyzing a part 830 in an exemplary embodiment. Imaging system 800 includes an ultrasonic wave generator 810, a sensor 811, and a signal processing unit 820. Signal processing unit 820 includes a backend interface 826 (e.g., an internal computer bus, Universal Serial Bus (USB), etc.) for providing instructions to generator 810. Signal processing unit 820 also includes frontend interface 828 (e.g., an Ethernet connection) through which reports may be transmitted, and display 821 (e.g., a screen) for displaying data to a user. Controller 822 controls the operations of imaging system 100. FIG. 8 further illustrates an exemplary part 830, which includes constituent material 834 (e.g., laminate of multiple plies of carbon fiber), an upper surface 832, and a lower surface 836.

In this example, part 830 has a uniform thickness of eighty plies of carbon fiber material. Part 830 is imaged by ultrasonic imaging system 800 in order to determine a porosity of part 830 (e.g., a number indicating what percentage of part 830 comprises hollow bubbles). To this end, ultrasonic imaging system 800 a confocal dual cavity laser interferometer (3.5 MHz) to image part 830. The interferometer includes sensor 811 (a cavity) and generator 810 (a laser). For each pixel (i.e., for each of multiple locations on part 830), imaging system 800 generates an ultrasonic wave and records amplitude and time-of-flight data. This results in an image of 400×400 pixels representing part 830.

The porosity of part 830 causes attenuation in the ultrasonic wave as it travels from front surface 832 to back wall 836. Thus, even though detection of the returning wave is gated to a time period when the wave is expected to return, the wave may be confused with a peak occurring during the gated period that is cause by random noise. Thus, it is possible that the amplitude value and time-of-flight values recorded for the ultrasonic wave represent noise, and not the desired signal of the returning ultrasonic wave.

To account for this problem and determine whether or not random noise dominates the image, controller 822 performs a statistical analysis of the image. The statistical analysis includes calculating the standard deviation of the time-of-flight data for the pixels of the image ($\sigma_{tof}$). In this example, the sample size comprises the time-of-flight values for the entire population of pixels.

Controller 822 also determines a standard deviation for a random sampling ($\sigma_r$) according to formula (1) below (setting N equal to the number of pixels used to calculate $\sigma_u$).

$$\sigma_r = \sqrt{\frac{1}{N}\sum_{i=1}^{N}(x_i - \mu)^2} \quad \text{where} \quad \mu = \frac{1}{N}\sum_{i=1}^{N}x_i \tag{1}$$

Controller 822 then divides $\sigma_r$ by a predefined constant (in this example, the number two) to calculate a threshold value. If $\sigma_{tof}$ is greater than the threshold value, this indicates that the time-of-flight values may be random. If the peaks sampled by imaging system 800 were sampled at substantially random times, it suggests that the peaks themselves (i.e., the amplitude values) are likely to be representative of mere random noise, instead of the desired ultrasonic wave. Thus, if $\sigma_{tof}$ is greater than the threshold value the image is flagged in memory 824 as invalid. However, if $\sigma_{tof}$ is less than the threshold value, then the peaks are more likely to represent the reflected ultrasonic wave. Thus, controller 822 utilizes the amplitude data for the image in order to calculate a porosity of part 830 and report the porosity to a user via display 821. Other calculations may be performed upon the amplitude and time-of-flight data to further quantify part 830 as desired.

Figure 9:
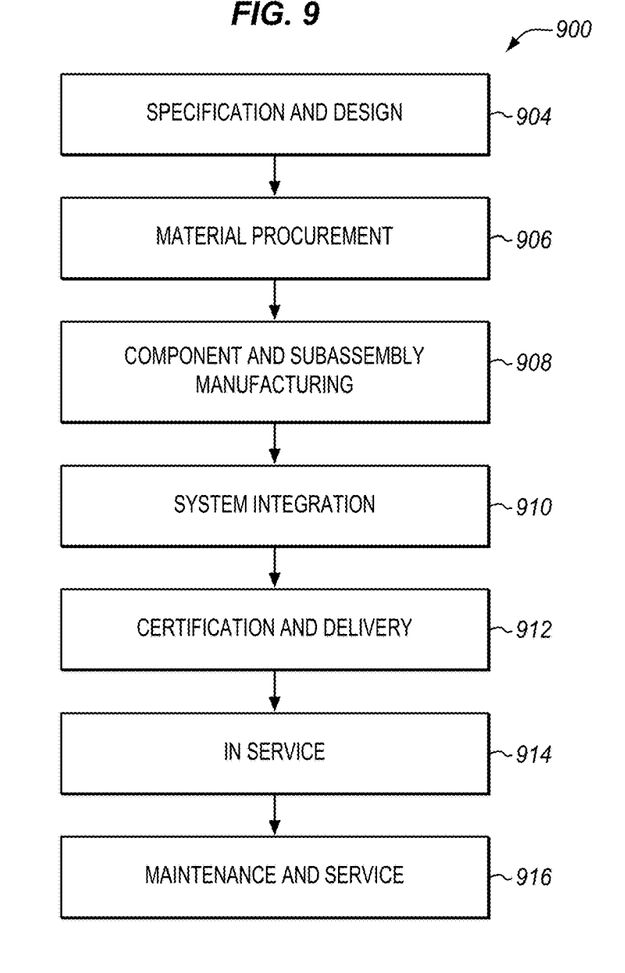
FIG. 9 is a flow diagram of aircraft production and service methodology in an exemplary embodiment.
Figure 10:
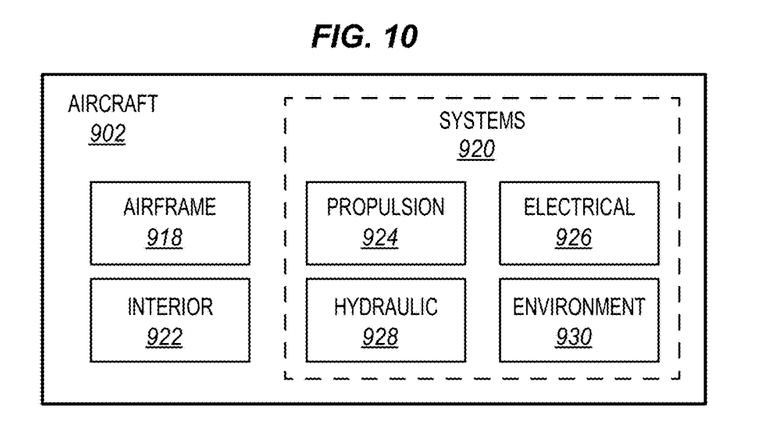
FIG. 10 is a block diagram of an aircraft in an exemplary embodiment.

Referring more particularly to the drawings, embodiments of the disclosure may be described in the context of an aircraft manufacturing and service method 900 as shown in FIG. 9 and an aircraft 902 as shown in FIG. 10. During pre-production, exemplary method 900 may include specification and design 904 of the aircraft 902 and material procurement 906. During production, component and subassembly manufacturing 908 and system integration 910 of the aircraft 902 takes place. Thereafter, the aircraft 902 may go through certification and delivery 912 in order to be placed in service 914. While in service by a customer, the aircraft 902 is scheduled for routine maintenance and service 916 (which may also include modification, reconfiguration, refurbishment, and so on).

Each of the processes of method 900 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 10, the aircraft 902 produced by exemplary method 900 may include an airframe 918 with a plurality of systems 920 and an interior 922. Examples of high-level systems 920 include one or more of a propulsion system 924, an electrical system 926, a hydraulic system 928, and an environmental system 930. Any number of other systems may be included. Although an aerospace example is shown, the principles of the invention may be applied to other industries, such as the automotive industry.

Apparatus and methods embodied herein may be employed during any one or more of the stages of the production and service method 900. For example, components or subassemblies corresponding to production stage 908 may be fabricated or manufactured in a manner similar to components or subassemblies produced while the aircraft 902 is in service. Also, one or more apparatus embodiments, method embodiments, or a combination thereof may be utilized during the production stages 908 and 910, for example, by substantially expediting assembly of or reducing the cost of an aircraft 902. Similarly, one or more of apparatus embodiments, method embodiments, or a combination thereof may be utilized while the aircraft 902 is in service, for example and without limitation, to maintenance and service 916. For example, the techniques and systems described herein may be used for steps 906, 908, 910, 914, and/or 916, and/or may be used for airframe 918 and/or interior 922.

In one embodiment, imaging system is utilized to analyze parts that comprise a portion of airframe 118 (e.g., a wing), in order to ensure that these parts meet with quality standards before, after, or during component and subassembly manufacturing 1108. For example, part 830 may be assembled into an aircraft in system integration 1110, and then be utilized in service 1114 until wear renders part 830 unusable. Imaging system 800 may be utilized for example to ensure that part 830 continues to conform with quality standards. Then, in maintenance and service 1116, part 830 may be discarded and replaced with a newly manufactured part 830. Thus, imaging system 800 may be utilized again in order to ensure that the new part 830 meets quality standards.

Any of the various elements shown in the figures or described herein may be implemented as hardware, software, firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, an element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments are described herein, the scope of the disclosure is not limited to those specific embodiments. The scope of the disclosure is defined by the following claims and any equivalents thereof.

The invention claimed is:

1. A system comprising:
an ultrasonic wave generator configured to induce ultrasonic waves at locations along a part being scanned; and
a controller configured to operate the ultrasonic wave generator to collect data points that each indicate amplitude data and time-of-flight data of an ultrasonic wave at the part, to calculate a standard deviation of the time-of-flight data of the data points ($\sigma_{tof}$), to utilize the amplitude data to quantify the part if $\sigma_{tof}$ is less than a threshold value, and to flag the data points in memory as including noise if $\sigma_{tof}$ is greater than the threshold value.

2. The system of claim 1 wherein:
the time-of-flight data indicates a time for an ultrasonic wave induced at a surface of the part to reflect off of a back wall of the part and return for detection;
the amplitude data indicates a magnitude of the ultrasonic wave; and
the controller is configured to determine that the amplitude data corresponds to random noise if $\sigma_{tof}$ is greater than the threshold value.

3. The system of claim 1 wherein:
the controller is configured to quantify a porosity of the part based on the amplitude data, and to update a memory to indicate the porosity of the part.

4. The system of claim 3 wherein:
the controller is configured to indicate that the part is out of tolerance in response to the porosity being outside of an acceptable range.

5. The system of claim 1 wherein:
the threshold value comprises a standard deviation of random noise ($\sigma_r$) divided by a predefined constant.

6. The system of claim 5 wherein:
$\sigma_r$ is calculated based on a sample size equal to the number of data points used to calculate $\sigma_{tof}$.

7. The system of claim 1 wherein:
the part comprises a multi-layer composite part.

8. A method comprising:
operating an ultrasonic wave generator to induce ultrasonic waves at each of multiple locations along a part being scanned;
collecting data points that each indicate amplitude data and time-of-flight data of an ultrasonic wave at the part;
calculating a standard deviation of the time-of-flight data for the data points ($\sigma_{tof}$);
utilizing the amplitude data to quantify the part if $\sigma_{tof}$ is less than a threshold value, and
flagging the data points in memory as including noise if $\sigma_{tof}$ is greater than the threshold value.

9. The method of claim 8 further comprising:
determining that the amplitude data corresponds to random noise if $\sigma_{tof}$ is greater than the threshold value.

10. The method of claim 8 further comprising:
quantifying a porosity of the part based on the amplitude data, and updating a memory to indicate the porosity of the part.

11. The method of claim 10 further comprising:
indicating that the part is out of tolerance in response to the porosity being outside of an acceptable range.

12. The method of claim 8 further comprising:
the threshold value comprises a standard deviation of random noise ($\sigma_r$) divided by a predefined constant.

13. The method of claim 12 wherein:
$\sigma_r$ is calculated based on a sample size equal to the number of data points used to calculate $\sigma_{tof}$.

14. The method of claim 8 wherein:
the part comprises a multi-layer composite part.

15. A system comprising:
a memory;
an interface; and
a controller configured to operate the interface to retrieve a scan representing a part that has been inspected via ultrasonic imaging, to populate the memory with time-of-flight data and amplitude data for each of multiple data points within the scan, to calculate a standard deviation of the time-of-flight data for the data points ($\sigma_{tof}$), to calculate a threshold value based on a standard deviation of random time-of-flight data, and to selectively perform signal processing on the data points by:
if $\sigma_{tof}$ is less than the threshold value: generating a report quantifying the part based on the amplitude data for the data points, and storing the report in the memory, and
if $\sigma_{tof}$ is greater than the threshold value: updating the memory to flag the scan as including noise.

16. The system of claim 15 wherein:
the time-of-flight data indicates time for a ultrasonic wave at a surface of the part to reflect off of a back wall of the part and return for detection;
the amplitude data indicates a magnitude of the ultrasonic wave after reflecting off of the back wall and returning; and
the controller is configured to determine that the amplitude data corresponds to random noise if $\sigma_{tof}$ is greater than the threshold value.

17. The system of claim 15 wherein:
the controller is configured to quantify a porosity of the part based on the amplitude data, and to include the porosity of the part in the report.

18. The system of claim 17 wherein:
the controller is configured to indicate that the part is out of tolerance in response to the porosity being outside of an acceptable range.

19. The system of claim 15 wherein:
the threshold value comprises a standard deviation of random noise ($\sigma_r$) divided by a predefined constant.

20. The system of claim 19 wherein:

$\sigma_r$ is calculated based on a sample size equal to the number of data points used to calculate $\sigma_{tof}$.

* * * * *